United States Patent [19]
Kranz

[11] Patent Number: 5,095,168
[45] Date of Patent: Mar. 10, 1992

[54] COLD TEMPERATURE ALKYLATION PROCESS

[75] Inventor: Ken Kranz, Kansas City, Mo.

[73] Assignee: Stratco, Inc., Kansas City, Mo.

[21] Appl. No.: 434,852

[22] Filed: Nov. 8, 1989

[51] Int. Cl.$^5$ .............................................. C07C 2/16
[52] U.S. Cl. .................................................. 585/730
[58] Field of Search ........................................ 585/730

[56] References Cited

U.S. PATENT DOCUMENTS

| | | |
|---|---|---|
| 3,170,002 | 2/1965 | Kelso .................................. 585/730 |
| 3,215,752 | 11/1965 | Vermilion ............................ 585/730 |
| 3,803,262 | 4/1974 | Goldsby ............................... 585/730 |
| 4,209,656 | 6/1980 | Prescott et al. ..................... 585/730 |
| 4,260,846 | 4/1981 | Karsay et al. ....................... 585/730 |
| 4,423,277 | 12/1983 | Stoud .................................. 585/730 |

Primary Examiner—Asok Pal
Attorney, Agent, or Firm—Shoemaker and Mattare, Ltd.

[57] ABSTRACT

A cold temperature alkylation reaction process, at −6° C. to 0° C., the production of isoparaffins useful as a high octane fuel additive derived from the reaction of $C_3-C_5$ olefins and isobutane in the presence of 92-95% sulfuric acid.

1 Claim, 5 Drawing Sheets

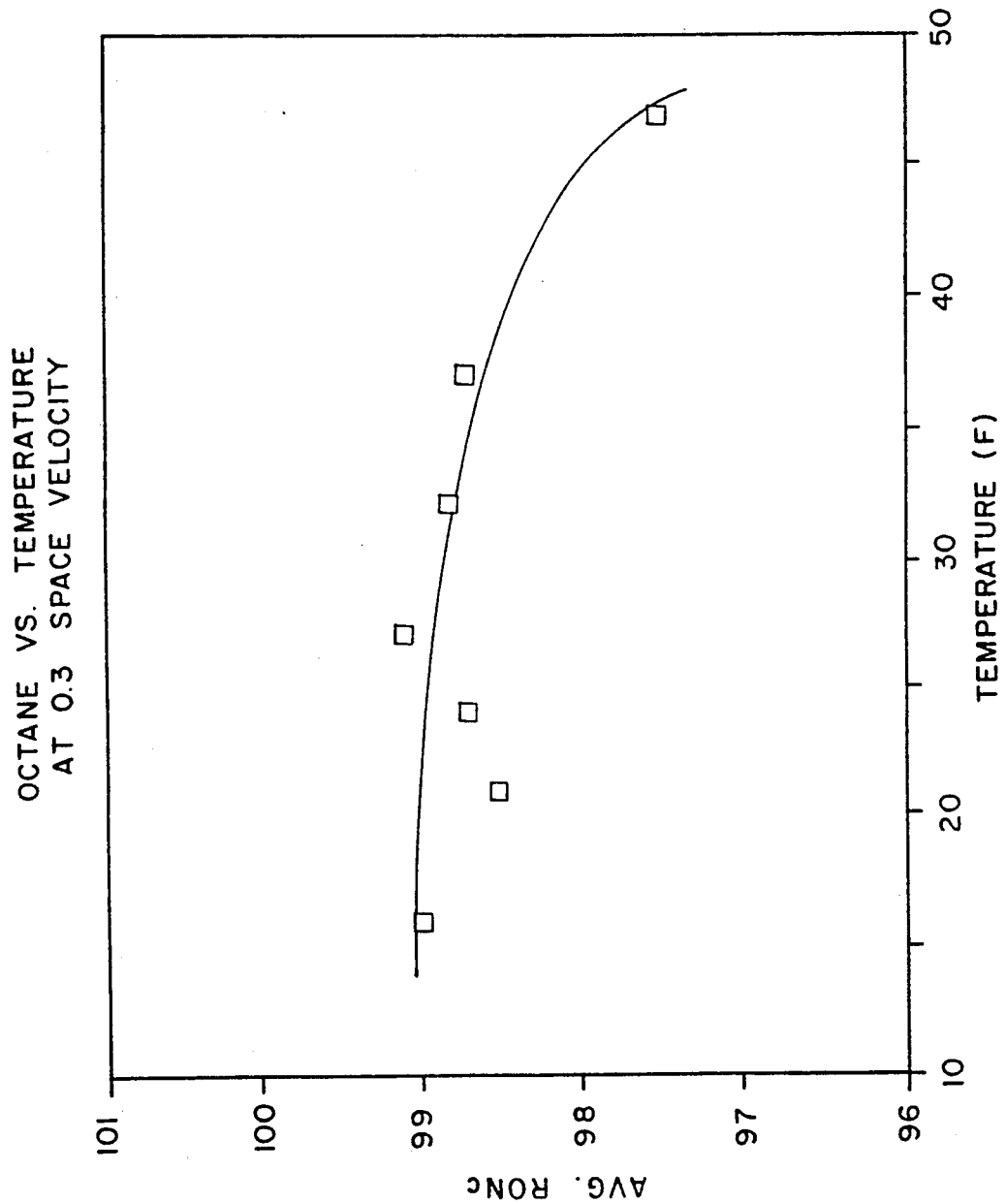

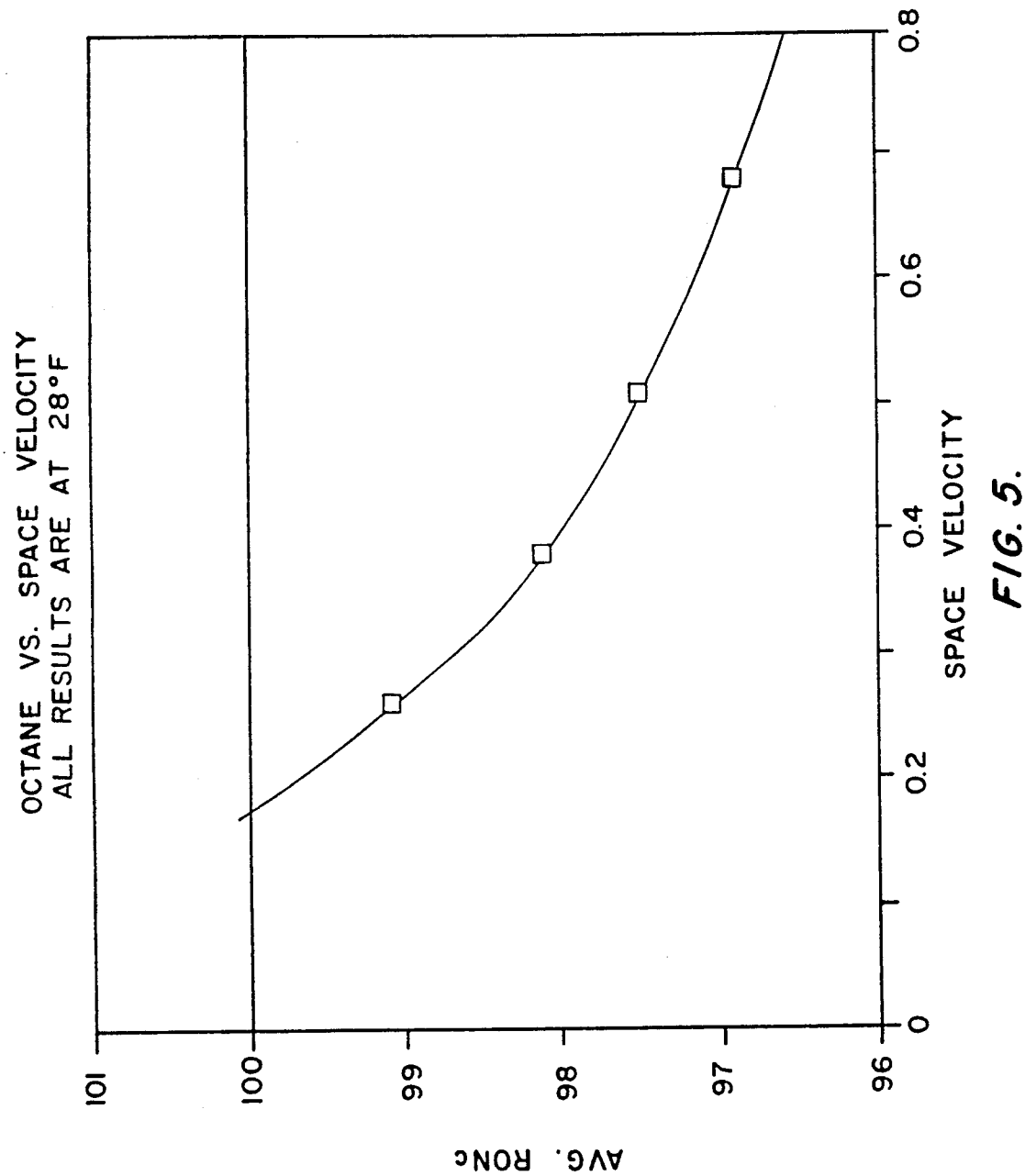

COLD TEMPERATURE ALKYLATION PROCESS

FIELD OF THE INVENTION

This invention relates to the alkylation of isoparaffinic hydrocarbons. More particularly, the invention concerns a one-step, cold temperature reaction process for the alkylation of isoparaffins with olefins in the presence of sulfuric acid to form branched chain paraffinic hydrocarbons capable of boiling in the gasoline motor fuel range and having enhanced anti-knock properties

BACKGROUND OF THE INVENTION

The alkylation of isobutane with light olefins such as propylenes and butylenes in the presence of either sulfuric or hydrofluoric acid is an important refinery process for producing high octane blending stock for gasoline. Hydrofluoric acid at room temperature and atmospheric pressure is a very corrosive gas. Recent desert tests of uncontrolled releases of hydrofluoric acid have proven that the dangers are much greater than previously thought. Sulfuric acid poses a much smaller risk to the population surrounding a refinery. Some refineries are considering converting from the hydrofluoric acid to sulfuric acid catalyst because of the safety issue. Current legislation limiting the use of lead as a gasoline octane booster has made the importance of selective and efficient alkylation even greater. Because of the increasing demand for higher octane gasoline blending stocks, refiners are constantly seeking ways to improve the operation of their alkylation units to increase their profitability. Because of the undesirable reactions occurring during the alkylation process, diluents called red oils or conjunct polymers dilute the acid catalysts reducing their efficiency as catalysts. Sulfuric acid is regenerated by burning the diluted or spent acid and recovering the SO2, oxidizing it to SO3, and reacting the SO3 with water to produce sulfuric acid. The cost of regenerating sulfuric acid is approximately 30% of the operating cost of the alkylation process. A method of reducing this operating cost while maintaining the quality of the alkylate product would improve the operation and economics of the alkylation unit.

SUMMARY OF THE INVENTION

In accordance with the present invention, an improved process is used to react $C_3$-$C_5$ olefins with isobutane in the presence of sulfuric acid. The reactor is maintained at preselected operating conditions to optimize the reactions taking place in a single reaction vessel to produce a high quality motor fuel alkylate and reduce dilution of the sulfuric acid catalyst. Specifically, the method includes the reaction of light olefins with isobutane in the presence of a sulfuric acid catalyst at temperatures lower than currently practiced to reduce undesirable side reactions which dilute the sulfuric acid catalyst while producing a high quality gasoline motor fuel alkylate containing predominately highly branched isoparaffinic hydrocarbons useful as a blending stock for gasoline. The conditions for the optimization are described more fully hereinafter.

BRIEF DESCRIPTION OF THE DRAWINGS

FIG. 4 is a graph of the effect of temperature on product RONc.

FIG. 5 is a graph of the effects of the spare velocity on produce RONc.

DETAILED DESCRIPTION OF THE INVENTION

Figure 1:
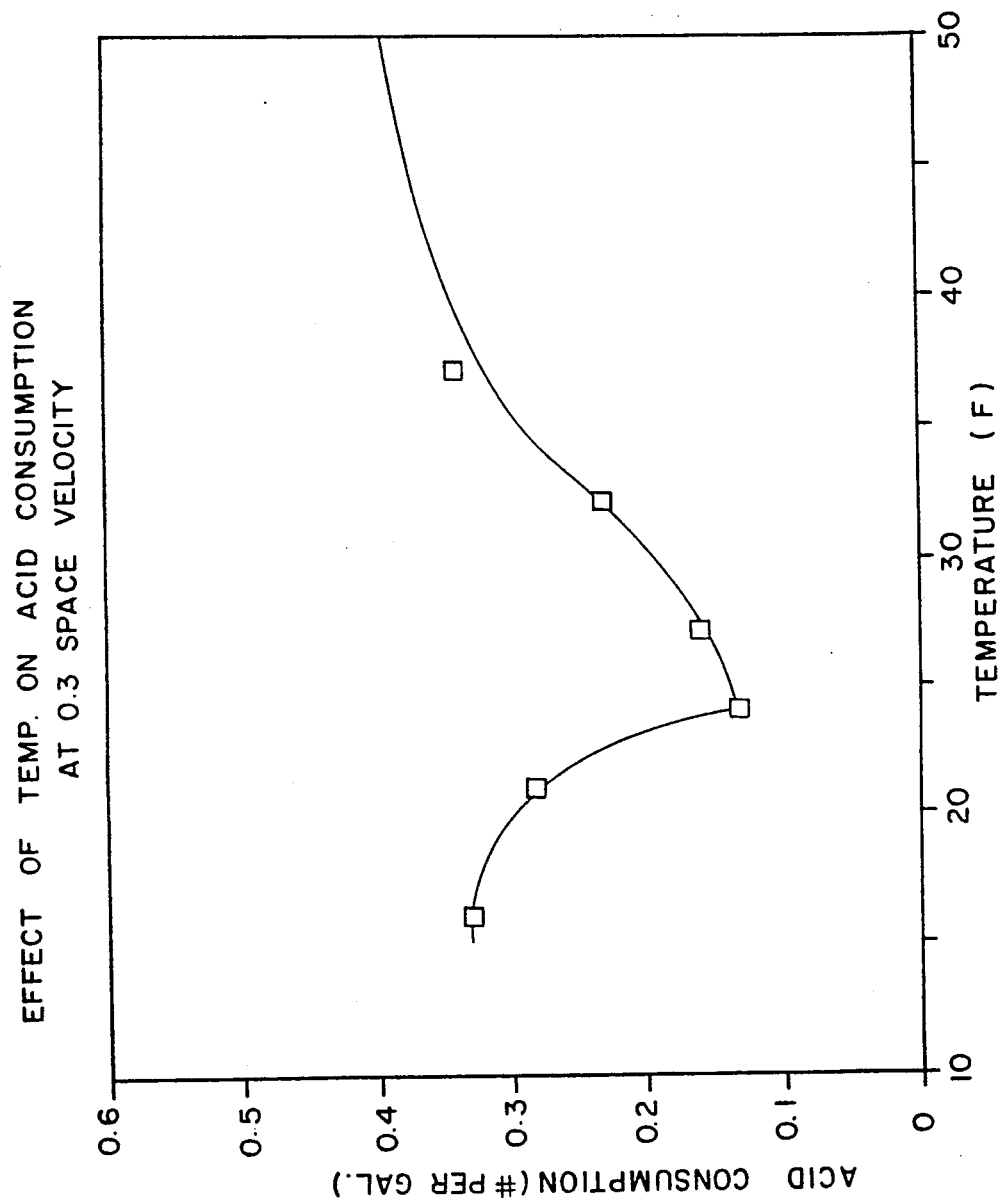
FIG. 1 is a graph of the effect of temperature on acid consumption.

In an embodiment of the present invention, a $C_3$-$C_5$ olefin containing hydrocarbon stream is contacted with sulfuric acid at temperatures below 38.F and preferably below 30° F. in a hydrocarbon/acid emulsion in which the $C_3$-$C_5$ olefins, preferably $C_4$ olefins, are reacted with a mixture of low molecular weight isoparaffins preferably isobutane, in the presence of sulfuric acid to obtain the desired alkylate product.

In this embodiment, the olefin-containing hydrocarbon stream and additional isobutane stream are contacted with sulfuric acid in the temperature range indicated at an acid-to-olefin molar ratio of from about 10 to about 25 to produce the desired alkylate reaction product.

The olefins which can be employed in the practice of the invention include any olefin having from 3 to 8 carbon atoms with the $C_4$ olefins preferred and 1-butene and 2-butenes being particularly preferred. The branched paraffinic hydrocarbons typically have from 4 to 8 carbon atoms with isobutane preferred. Typically, the branched paraffin is obtained by the distillation and/or cracking of petroleum oils and of other hydrocarbonaceous oils which are recovered as side streams or fuel gas streams. Preferably, the isoparaffinic hydrocarbons have been segregated as by fractionation.

In a conventional sulfuric acid alkylation process, olefins are reacted with isobutane at 5°-20° C. to form highly branched C5+ hydrocarbons, primarily dimethylpentanes and trimethylpentanes. Typical overall alkylation reactions for propylene and 2-butene are:

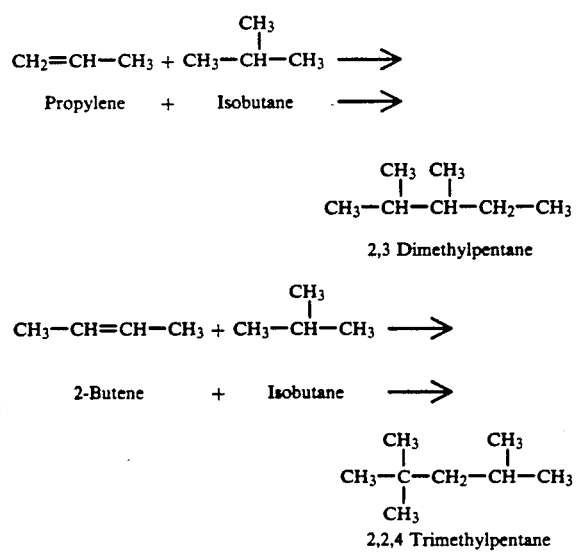

In the conventional process and that contained in this invention, the olefins are combined with an excess amount of isobutane and are fed to a reactor containing an emulsion of sulfuric acid and hydrocarbons. The acid and hydrocarbon phases of the emulsified mixture leaving the reactor are separated typically by gravity settling. The acid is recycled back to the reaction zone, and the hydrocarbon reactor effluent is separated by distillation or stripping into the respective product streams. The isobutane in the reactor effluent stream is recovered and recycled to the reaction zone. Typical prior art processes are described in U.S. Pat. Nos. 3,000,994 and 3,227,774, and Canadian Patent No. 446,901.

Ideally, the sulfuric acid, acting as a catalyst, serves to promote the alkylation reaction without being consumed. In actuality, competing side reactions occur and the presence of certain feed impurities consume or dilute the acid. In order to maintain the acid strength in these conventional single stage alkylation units above about 88-90 wt % $H_2SO_4$, fresh sulfuric acid of about 98 to 99 wt % $H_2SO_4$ must be added to the reaction zone when spent acid is withdrawn. Some refineries continuously withdraw used acid and add fresh acid as make-up; other refineries withdraw and add the acids intermittently. The spent sulfuric acid is regenerated by a facility at the refinery site or shipped to a regeneration facility where it is burned, the $SO_2$ vapors oxidized to $SO_3$, and then combined with water to produce fresh 98 to 99 wt % sulfuric acid.

With conventional sulfuric acid alkylation, the reaction zone conditions that promote the alkylation reactions and minimize side reactions are:

1) improved mixing;
2) decreased temperatures when operating in the range of about 5° C. to 25° C. which is the range of current commercial practice;
3) higher isobutane concentration;
4) larger acid volume in reactor (lower olefin space velocity);
5) lower feed contaminant concentrations; and
6) lower residence time of acid in the in acid settler.

In addition, the composition of the sulfuric acid will affect the octane number (or quality) of the product and acid consumption. Maximum octane numbers are obtained at acid strengths of 93 to 94 wt % $H_2SO_4$ with water concentrations of 0.5 to 1 wt %[1].

[1] Albright, L. F., Houle, L., Sumtka, A. M., and Eckert, R. E., "Alkylation of isobutane with Butenes: Effect of Sulfuric Acid Compositions", *Ind. Eng. Chem. Process Des.* 11, 446 (1972).

The preferred feed is $C_4$ olefins with n-butenes being especially preferred to produce high quality alkylates and low acid consumption when the alkylation process of the present invention is operated under the described operating conditions. The acid consumption is much lower and the alkylation products produced have higher octane numbers than the same olefins reacted at higher temperatures.

As previously described, the desired result of the alkylation of isobutane and light olefins is to produce a hydrocarbon product with a high octane number while maintaining or reducing sulfuric acid consumption or dilution with conjunct polymers which can occur as the result of undesirable side reactions. Consumption of the sulfuric acid in commercial operations is a large cost (approximately 30%) of the overall process costs. As far as product quality is concerned, an improvement of one-half octane number is significant. Higher quality alkylate products allow refineries to add less hydrocarbons such as reformate, which contain benzene, or permit reducing the addition of ethanol to the gasoline pool in order to maintain the octane rating. At this time, it appears that the alkylation process of the present invention described herein can significantly improve the product quality and reduce sulfuric acid consumption.

The following experiments were conducted to evaluate the use of temperatures colder than presently used in single-stage commercial alkylation schemes.

Bench scale equipment was used for this study. This includes a 450 ml stirred reactor. The mixer speed for this reactor is maintained at about 1100 rpm.

A five gallon water cylinder was pressured to approximately 120 psi with nitrogen. The water flows from the water cylinder through a flowmeter and into the bottom of a cylinder of mixed isobutane/olefin feed. The hydrocarbon feed was fed through a molecular sieve to remove water from the feed, and then into the reactor. Effluent was drawn off the bottom of the reactor and then directed to a settler. Acid is drawn from the bottom of the settler and recirculated back to the reactor. The hydrocarbon product flows from the top of the settler through a caustic bed, and into the product cylinder.

A large batch of synthetic used sulfuric acid was prepared by first spiking fresh acid with oleum to raise the acidity to 98.5-99% $H_2SO_4$. Butene-1 was then bubbled through the acid until the acidity is reduced to approximately 97.5% $H_2SO_4$. Then 2-butenes are bubbled through the acid until an acidity of 94.5-95% $H_2SO_4$ is obtained.

The system described was then charged with 500 ml of synthetic used acid prepared as directed. An average acid to hydrocarbon volume ratio in the reactor of 45 to 65% was maintained throughout the runs. Usually the acid to hydrocarbon ratio was maintained at 50-55% (v/v). The settler temperature was monitored in the middle of the settler and where the acid exits. The temperature of the middle of the settler was kept at or below the reactor temperature while the temperature of the acid exiting the settler is always about 5 degrees warmer.

A sample of acid and product was analyzed about every 1.5 hours. The acid was sampled by purging 5 ml of acid through a sampling valve and collecting it in a centrifuge tube. The acid sample was then centrifuged for 15 minutes and about 0.5 g (weighed to +/−0.1 mg) was titrated to the methyl red end point with standardized NaOH. The alkylate samples were analyzed by a standard gas chromatograph (G.C.) procedure. The G.C. was equipped with a 50 m capillary column which could separate up to C14 hydrocarbons.

Using the previously described reaction scheme, the following results were observed.

It was found that by maintaining the temperature of the reactor within a predetermined temperature range, the acid consumption was greatly reduced. This optimum temperature range was found to be between about 20° and 30° F. (−6° C. and −1° C.). The quality of the alkylate product was also improved by operating at lower than normal temperatures. FIG. 1 shows the optimum temperature of the reactor to be in the mid 20° F. range. Increased acid consumption below a certain temperature is an unexpected result. It is generally assumed in the industry and in the art that as the temperature is lowered, the acid consumption will continue to decrease. It is not completely understood why the acid consumption started to increase when the reactor temperature was less than 24° F.

To more completely test the benefit of the optimum temperature range, a set of two extended laboratory experiments were conducted. The flow rate of the reactants was doubled in order to operate under more severe conditions and to reduce the time of the experiments. These extended experiments show the performance of an alkylation process of the present invention throughout the acidity range used in the industry. The feed composition for these two extended laboratory experiments was 0.30 wt % propane, 86.14 wt % isobutane, 1.93 wt % n-butane, 3.92 wt % 1-butene, 4.07 wt % t-2-butene, and 3.60 wt % C-2-butene.

Figure 2:
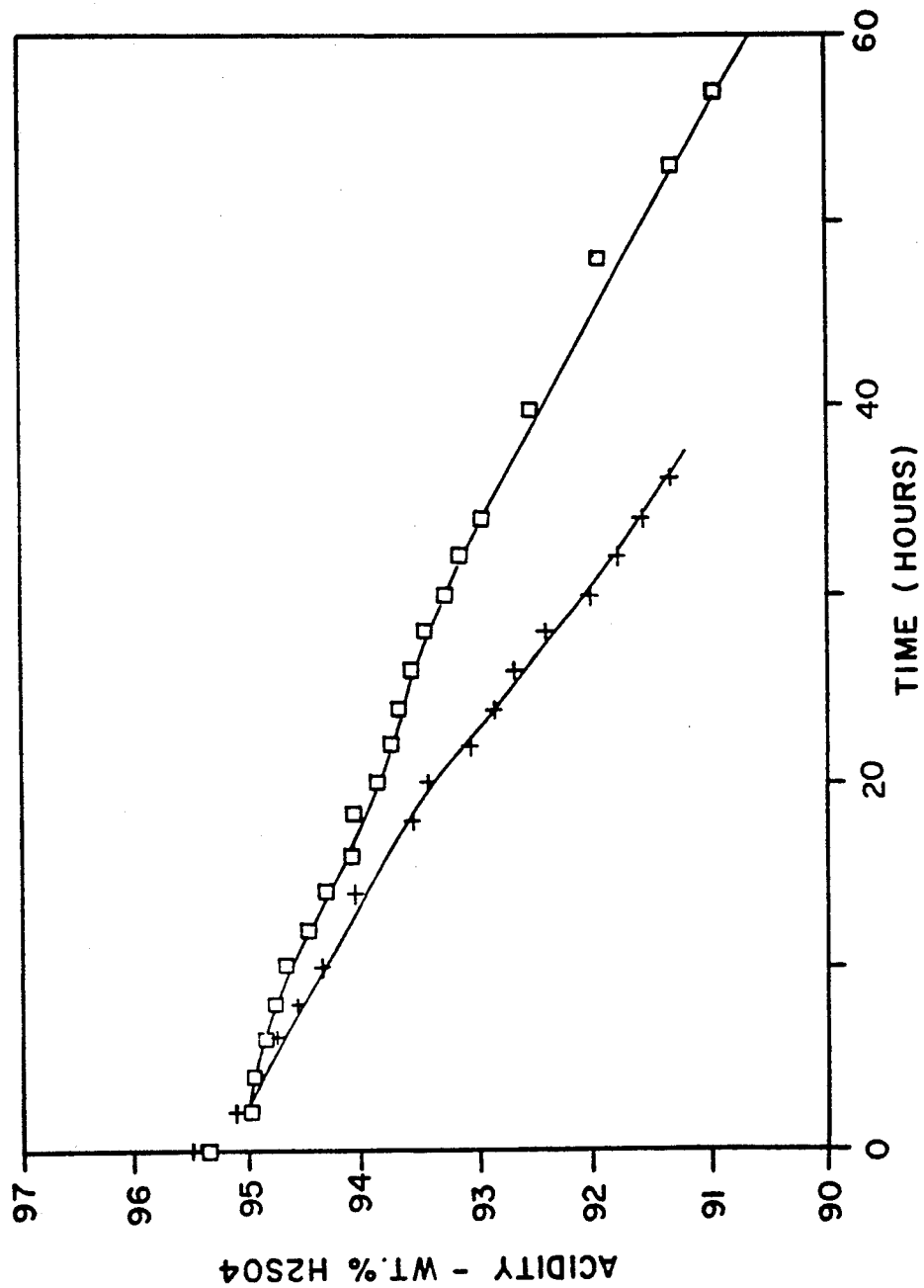
FIG. 2 is a graph of the acid strength decline as a function of time at 28° F. and 49° F. reaction temperatures.
Figure 3:
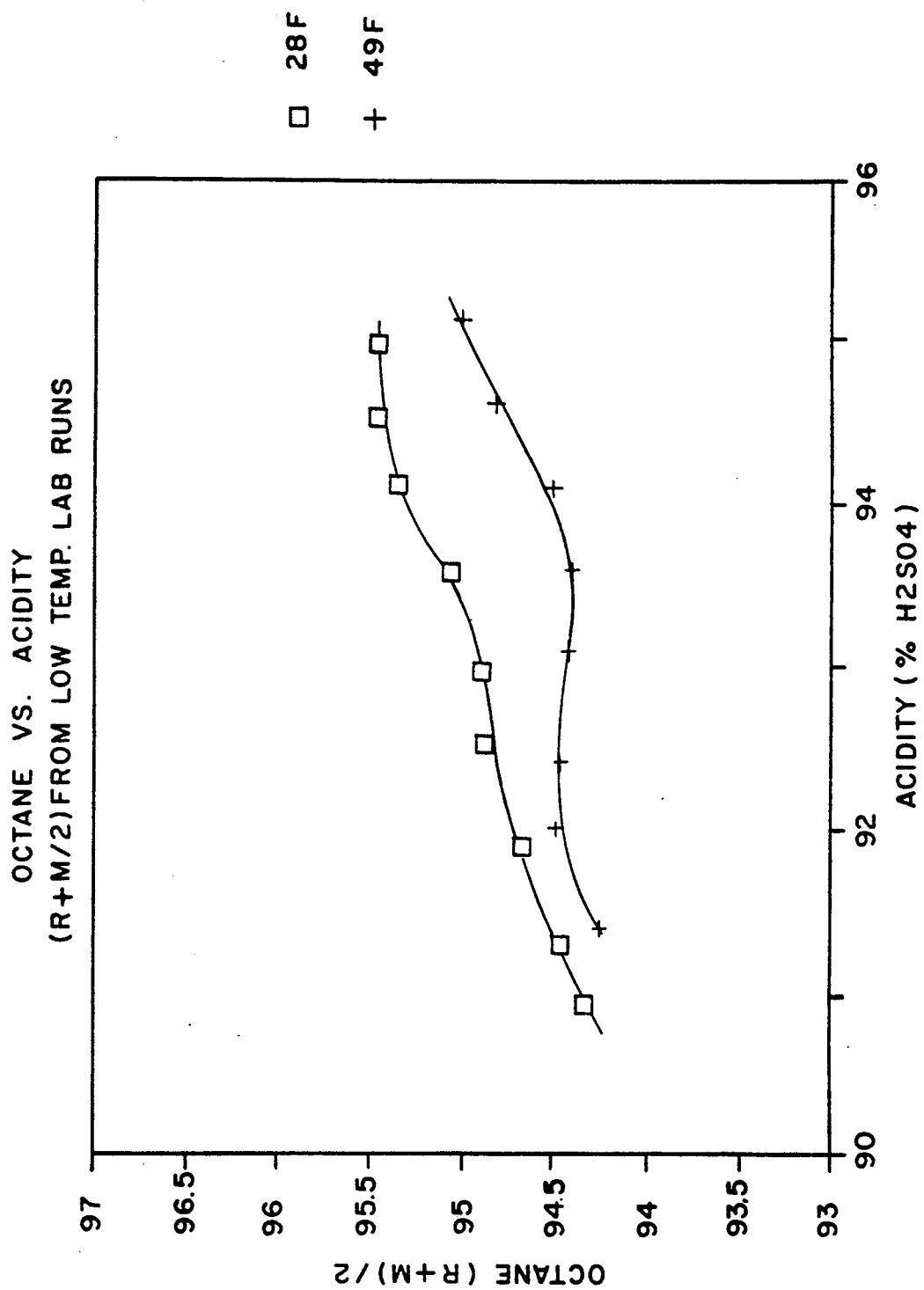
FIG. 3 is a graph of the effect of acid strength on product octane at 28° F. and 49° F. reaction temperatures.

The graphs in FIGS. 2 and 3, respectively, are from the extended experiments which compares a conventional alkylation experiment conducted at a typical temperature (49° F.) and a cold temperature experiment (28° F.). The graph in FIG. 2 indicates acid consumption and the graph in FIG. 3 shows the product quality.

The colder reaction temperature of the reactor did result in a significant decrease in acid consumption. This is shown in the graph in FIG. 2 entitled $H_2SO_4$ use study comparing acidity vs. time. Constant acid consumption would result in a gradual downward curve due to a decreasing inventory of acid in the system. The slope of the curve is proportional to the acid consumption in that the steeper the curve, the greater the acid consumption.

Acid consumption values are based on a 98.5%–90% spending range (98.5% fresh acid fed in, and 90% acid withdrawn). Average acid consumption values do not include that during the first 2 hours. The 28° F. run averaged 0.197 #/gallon alkylate produced while the 49° F. run averaged 0.323 #/gallon alkylate produced which is about a 40% reduction in sulfuric acid consumption. Many commercial alkylation units average 0.4–0.6 #/gallon acid consumption.

The 28° F. process of the present invention gave about a half an octane number higher quality alkylate than the 49° F. run. Lowering the reaction temperature from 49° F. to 28° F. resulted in isoparaffins containing less lights and more heavies being produced with the same amount of C8's. The octane increase of the lower temperature appears to be from a decrease of 2,2,4-TMP and an increase of higher octane 2,3,4- and 2,3,3-TMP isomers.

FIG. 4 shows the effect of reactor temperature on product quality. It shows that as reactor temperature decreases, the octane generally increases. The largest increase in octane seems to occur as the temperature decreases from 50° to 35° F.

FIG. 5 demonstrates the relationship of space velocity on octane of the alkylate. Space velocity is a measure of the throughput or residence time in the reactor.

As previously mentioned, the extended laboratory runs were conducted at a space velocity of 0.6 to double the recommended production rate. Even at this high rate, the cold process of the present invention produced a high quality product with low acid consumption or dilution of the $H_2SO_4$. It can be seen that by using the process described herein, a refinery could increase the production rate of an alkylation unit and maintain or even improve the quality of alkylate product and consumption of the $H_2SO_4$ acid catalyst.

A factor to consider in evaluating the overall performance of any process is the extra production costs associated with running an alkylation process at colder than "normal" or previously employed temperatures. A savings in acid consumption at lower temperatures will help offset the increased refrigeration costs. If the acid consumption is lowered by about 0.15 lbs. per gallon, the extra refrigeration costs can be offset based on current electricity costs and acid regeneration costs. In summary, it appears that the process of the present invention is economically feasible in this regard. The process operates very well in the acidity range currently used in the industry.

At the preferred conditions of the alkylation process of the present invention, the isooctanes ($iC_8H_{18}$) produced are a mixture that are predominantly trimethylpentanes which as a mixture have research octane numbers (RON) values of about 102 to 103. Relatively small amounts of light ends ($C_5$–$C_7$ isoparaffins), dimethylhexanes (DMH's) and heavy ends ($C_9$ and heavier isoparaffins) are produced as by-products.

The present invention has been described herein in its preferred embodiments. It will be appreciated, however, that many alternative materials and methods can be employed within the teachings contained herein to produce some or all of the advantages shown and that these alternatives are encompassed within the scope of the claims as limited only by the application of pertinent prior art.

I claim:

1. A method for the production of isooctanes during the alkylation of isobutane with an olefinic hydrocarbon selected from the group consisting of 1-butene, cis-2-butene, trans-2-butene and isobutylene in the production of high quality motor fuel having an octane rating of greater than about 95, said method comprising:
   (a) contacting in a reaction vessel the selected olefinic hydrocarbon and isobutane with sulfuric acid having a concentration of from about 92% to about 95.0%; and an acid-to-olefin molar ratio is from about 10 to about 25;
   (b) maintaining said reaction vessel at a temperature of about from about 0° C. to about −6° C. with a space velocity of less than about 0.6;
   (c) subsequently removing alkylate reaction product from said reaction vessel wherein isooctanes produced are a mixture predominantly comprising trimethyl-pentanes.

* * * * *